United States Patent
Jones et al.

(10) Patent No.: US 8,524,958 B2
(45) Date of Patent: Sep. 3, 2013

(54) PROCESS FOR PREPARATION OF OLIGOMERIC OR POLYMERIC COMPOUNDS USING SELECTIVE MICHAEL ADDITION

(75) Inventors: Richard M. Jones, Oak Ridge, NJ (US); Steven H. Nahm, Loveland, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 612 days.

(21) Appl. No.: 12/665,748

(22) PCT Filed: Jun. 13, 2008

(86) PCT No.: PCT/US2008/066827
§ 371 (c)(1),
(2), (4) Date: Sep. 16, 2010

(87) PCT Pub. No.: WO2009/002726
PCT Pub. Date: Dec. 31, 2008

(65) Prior Publication Data
US 2011/0015343 A1    Jan. 20, 2011

Related U.S. Application Data

(60) Provisional application No. 60/946,017, filed on Jun. 25, 2007.

(51) Int. Cl.
*C08L 61/00* (2006.01)
*C08G 16/00* (2006.01)

(52) U.S. Cl.
USPC .............. 585/16; 524/877; 528/220; 528/230

(58) Field of Classification Search
USPC .......................................................... 585/16
See application file for complete search history.

(56) References Cited

U.S. PATENT DOCUMENTS

| | | | |
|---|---|---|---|
| 5,017,649 A | 5/1991 | Clemens | |
| 5,034,536 A | 7/1991 | Fazio | |
| 5,096,940 A | 3/1992 | Mor | |
| 6,461,735 B1 | 10/2002 | Furuya et al. | |
| 6,933,078 B2 | 8/2005 | Huang et al. | |
| 7,271,204 B2* | 9/2007 | Fechter et al. | 522/174 |
| 7,396,429 B2* | 7/2008 | Beckley et al. | 156/275.7 |
| 7,473,734 B2* | 1/2009 | Beckley et al. | 525/54.2 |
| 7,705,064 B2* | 4/2010 | Jacobine et al. | 522/36 |
| 7,855,262 B2* | 12/2010 | Nahm | 526/319 |
| 7,888,442 B2* | 2/2011 | Nahm | 526/319 |
| 7,985,809 B2* | 7/2011 | Krawczyk et al. | 525/529 |
| 2005/0043541 A1 | 2/2005 | Walter et al. | |
| 2005/0245636 A1 | 11/2005 | Fechter et al. | |

(Continued)

OTHER PUBLICATIONS

International Search Report and Written Opinion of the International Searching Authority, issued for corresponding PCT Application No. PCT/US2008/66827, dated Aug. 26, 2008.
Kanemasa et al.: "Stereoselective Michael Addition of the Imines of alpha-Amino Esters in the Presence of Lithium Bromide/1,8-Diazabicyclo[5.4.0]undec-7-ene", Journal of Organic Chemistry, American Chemical Society, vol. 55, No. 14, Jan. 1, 1990, pp. 4411-4417, XP002607994.

(Continued)

*Primary Examiner* — Ellen McAvoy
(74) *Attorney, Agent, or Firm* — Kramer Levin Naftalis & Frankel LLP (57) ABSTRACT

A method of preparing an oligomeric or polymeric compound in a liquid solution is disclosed which consists of reacting a Michael donor compound with a Michael acceptor compound in the presence of a first catalyst and a Group IA and/or Group IIA metal ion catalyst.

30 Claims, 2 Drawing Sheets

(56) References Cited

U.S. PATENT DOCUMENTS

| | | |
|---|---|---|
| 2006/0079645 A1 | 4/2006 | Hasegawa et al. |
| 2006/0247374 A1 | 11/2006 | Beckley et al. |
| 2006/0264594 A1 | 11/2006 | Nahm |
| 2006/0270801 A1 | 11/2006 | Hagiopol et al. |
| 2007/0173602 A1* | 7/2007 | Brinkman et al. ............ 524/592 |
| 2009/0275713 A1* | 11/2009 | Shah et al. .................... 526/130 |
| 2010/0068393 A1* | 3/2010 | Bowman ....................... 427/331 |
| 2011/0251338 A1* | 10/2011 | Kim et al. ..................... 524/559 |

OTHER PUBLICATIONS

Mather et al. "Michael addition reactions in macromolecular design for emerging technologies", Progress in Polymer Sceince, Pergamon Press, Oxford, GB, vol. 31, No. 5, May 1, 2006, pp. 487-531, XP025078607.

* cited by examiner

PROCESS FOR PREPARATION OF OLIGOMERIC OR POLYMERIC COMPOUNDS USING SELECTIVE MICHAEL ADDITION

CROSS-REFERENCE TO RELATED APPLICATIONS

The present application is the United States national phase filing of corresponding international application number PCT/US2008/66827, filed on Jun. 13, 2008, which claims priority to and the benefit of U.S. provisional application Ser. No. 60/946,017, filed on Jun. 25, 2007, the disclosure of which is being incorporated by reference herein.

FIELD OF THE INVENTION

The invention relates to a process of preparing oligomeric or polymeric compounds of much lower polydispersity by Michael addition in the presence of Group IA and/or Group IIA metal ions thereby selectively favoring monoaddition of methylene functional Michael donor compounds to Michael acceptor compounds.

BACKGROUND OF THE INVENTION

Formation of enolate ions and their Michael addition to unsaturated molecules containing electron-withdrawing groups are key reactions for generation of carbon-carbon bonds in a variety of applications (Carruthers et al., Modern Methods of Organic Synthesis, Cambridge University Press (0521778301)). Considering the present interest in "green" processes (Jackson, Adhesives and Sealants Industry, Apr. 2006, 20-25), Michael additions have many attractive attributes when one can avoid solvents and use catalytic amounts of base. These reactions maximize atom economy, are largely made from natural feedstocks (with the current exception of acrylic acid), and are readily degraded by ester hydrolysis in the environment.

Acrylated oligomers with high functional density are useful starting points for making structured Michael addition products. To be most useful, the products from addition to these oligomers must not create formulated viscosities that are too high to be applied by the usual coating means. For example, in the printing industry using flexography, the final ink viscosity must be less that 1 Pa·s. The use of solvents for the purpose of viscosity reduction is limited due to VOC or migration restrictions in packaging applications of such inks. Thus is it preferable to make structures with low intrinsic viscosity and Newtonian flow under shear.

The most common Michael donors are acetoacetyl esters with two acidic CH bonds (a methylene) between the carbonyl groups. To avoid high polymer and gelation in the base-catalyzed addition to polyacrylates at close to stoichiometric 1:1 equivalents ratio, there is a need to control the reaction of these two sites such that only the enolate derived from the methylene reacts with the Michael acceptor to the exclusion of the enolate from the methine formed after the first addition. While this is the order expected by thermodynamics (pKa typically 11 and 13, respectively), the most common result is dialkylation when stoichiometric ratios of donors and acceptor functions are used (approximately one mole of methylene donor to one equivalent of olefin acceptor) under basic conditions (either stoichiometric or catalytic base). Our attempts to vary the basicity of the medium to select between the two acids only resulted in the expected rate change but without any appreciable effect on product selectivity.

It has been proposed that the monomeric enolate ion pairs are the reactive species in addition and substitution reactions (Zaugg, J. Ratajczyk, J. Leonard, and A. Schaefer, J. Org. Chem., 37(14), 2249-2253 (1972)). Aggregation decreases as the degree of substitution increases (Streitwieser, Y. Kim, and D. Wang, Organic Letters, 3(16), 2599-2601 (2001)). Thus while the substituted (methine) enolate is less favored by thermodynamics, the Michael product from it may be more likely to form due to the higher than expected concentration of the corresponding monomeric mono-substituted ion. This proposal is supported in experimental data on lithium enolates in THF solvent (Facchetti et al. J. Org. Chem., 69, 8345-8355 (2004)).

In contrast, it has also been proposed that polyalkylation is favored by aggregation of the enolate (House, M. Gall and H. D. Olmstead, J. Org. Chem. 36, 2361-2371 (1971)). There are many publications that demonstrate that the order of increasing aggregation is $R_4N+ \sim K+ < Na+ < Li+$. According to this mechanism, one would not expect enolates with $Na+$ or $Li+$ counterions to be especially capable of very high selectivity for monoalkylated products in the catalyzed Michael addition of acetoacetyl esters to polyacrylate acceptors. This statement is supported by the following experimental evidence.

Clemens et al. (61(770), 83-91 (1989)) discloses information concerning the effect of base identity on the ratio of bis- to mono-alkylation in the Michael addition of isobutyl acetoacetate to ethyl acrylate. Here, the selectivity observed is attributed to the nature of the base, e.g., hydroxide versus amidine. No observation of an effect of the enolate counterion is reported.

In a paper by Iwamura et. al. (Tetrahedron Letters, 46, 6275-7 (2005)) on the addition to a monoacrylate of the enolate formed using KOH base from a sterically hindered acetoacetate at 3/2 equivalents ratio, respectively, the result is predominately di-addition even at low temperature.

Bonadies et. al. (Gazetta Chimica Italiana, 124, 467-468 (1994)) reports excellent yields of conjugate addition to methylvinylketone using LiOH catalyst in dimethoxyethane (DME) solvent. But since both ethyl acetoacetate and ethyl 2-ethylacetoacetate give rapid rates of addition under the same conditions, no specific control of Michael polyaddition would seem possible under these conditions.

Ye et al. (Tetrahedron Letters, 46, 6875-8 (2005)) reports that guanidine bases give a high yield of monoaddition with dimethyl malonate and cyclopent-2-en-1-one in toluene solvent.

U.S. Pat. No. 5,667,901 describes products from use of 1:1 equivalents and higher of acetoacetate esters in Michael addition with TMPTA catalyzed by sodium methoxide. Both structures from monoaddition and diaddition are characterized in this document as products of reaction.

In summary, there is a long-standing problem with polyalkylation in Michael addition of methylene enolate anions (donors) to carbonyl-activated olefins (acceptors) that can generate a complex mixture of products. Various means have been proposed to address this problem.

The simplest is the inclusion of protic acid solvents of pKa intermediate between the methylene and methine protons of the unsubstituted and monosubstituted 1,3-dicarbonyls, respectively (e.g., the effect of butyl alcohol in a DBU-catalyzed reaction of ethylacetoacetate in Graham et al. (Water-Borne, High Solids, and Powder Coatings Symposium, Feb. 24-26, 1993). To the extent that this could be successful given only a two pK unit difference in acidity and the large number of competing processes (transesterification, alcohol addition, and reverse Claisen) as can proceed with alcohols, the requirement for volatile solvent limits its application.

Other disclosed procedures use formation of complex organometallics such as from the reaction of an enolsilane with a Lewis acid (reviewed in Reetz et al., Tetrahedron Letters, 34(46), 7395-8 (1993)), formation of an amine-manganese complex (Cahiez et al., Tetrahedron Letters, 35(19), 3065-8 (1994)), or formation of an alkyl zinc compound (Morita, M. Suzuki, R. Noyori, J. Org. Chem., 54, 1787-8 (1989)). However, these also require specialized solvents and conditions or leave objectionable metals in the product unless additional steps are taken.

More effectively, an activating ester group can be introduced by Claisen condensation followed by its removal by decarboxylation after alkylation (Caine, Comprehensive Organic Synthesis, B. Trost and I. Fleming, eds., Vol. 3, p. 1, Pergamon Press, Oxford, 1991). However, there are at least two additional steps that limit construction of an efficient process.

The problem becomes even more acute when it is desired to use poly-unsaturated Michael acceptors (e.g., trimethylolpropane triacrylate, TMPTA) where rapid generation of high molecular weight by branching through extensive dialkylation at stochiometries near 1:1 equivalent ratios can gel reactors. To avoid these gels, large excesses of either donor or acceptor functions can be used to make oligomers (10 to 1000 Pa·s. at 25° C.) in a soluble, strong base-catalyzed process (U.S. Pat. Nos. 5,569,779; 5,536,872; 5,430,177; 5,350,875; 5,347,043; 6,706,414 B1; 6,025,410; WO 01/00684 A1; U.S. Pat. No. 5,945,489). These products by necessity include unreacted starting donor or acceptor molecules that limit the chemist's options in the use of these materials. And if reaction is carried beyond 50% consumption of either component in excess (just short of the gel point as measured in Clemens et al. (61(770), 83-91 (1989)), large amounts of diluent must be added to restore viscosities for such products to be useful as lubricants and coatings.

In a parallel development, monofunctional reactants in admixture with polyfunctional reactants can function as chain terminating groups in these addition polymerizations, limiting the opportunities of extension to higher molecular weight (EP 1 431 320; U.S. Pat. No. 6,897,264; and U.S. Pat. No. 6,855,796). This approach needs at least one equivalent of monofunctional donor or acceptor to block roughly half of the polyfunctional acceptor or donor sites. Use of monofunctional donors or acceptors limits the number of remaining acceptor or donor functions, respectively, that can be used in a subsequent reaction.

The products from either of these above classical approaches to limiting molecular weight are still characterized by a high degree of shear-thinning coming from entanglement of the linear and branched segments present in the fraction of very high molecular weight that remains even in short-stopped products of these processes.

Clearly, based on the above, there is no indication in the prior art that anyone recognized the importance of increased ion-pairing to methylene enolate monoaddition. In addition, there remains a need to control the reaction of multi-functional Michael donors with multi-functional acceptors at stoichiometric ratios near 1:1 equivalents to minimize polydispersity and molecular weight together with maximization of final functionality.

SUMMARY OF THE INVENTION

The present invention provides a method of preparing an oligomeric or polymeric compound in a liquid solution comprising reacting a Michael donor compound containing at least one acidic methylene group with an unsaturated Michael acceptor compound containing more than one unsaturated group in the presence of a first catalyst and a Group IA and/or Group IIA metal ion catalyst, wherein said first catalyst does not comprise said metal ions.

The present invention also provides oligomeric or polymeric compounds prepared according to the method of the present invention.

Other objects and advantages of the present invention will become apparent from the following description and appended claims.

DETAILED DESCRIPTION OF THE INVENTION

It has been surprisingly discovered that the addition of Group IA or Group IIA metal ions in catalytic amounts to a base-catalysed Michael Addition reaction allows for a more selective addition of methylene donor compounds to acceptor compounds. The Michael Addition reaction may also be carried out in the presence of catalysts that are not strongly basic and do not contain the above Group IA or Group IIA metal ion(s). Examples include phosphenes such as Trioctylphosphine (TOP) and phase transfer salts such as Methyltributylammonium chloride (MTBAC). Each of these systems transform from low selectivity, high polydispersity to high selectivity, low polydispersity with the addition of Group IA or Group IIA metal ion-containing salts.

The catalysts and process of the present invention address all the shortcomings discussed above in an efficient manner to yield highly symmetrical, liquid, functional products from near 1:1 equivalent ratios without objectionable metals, solvents, or large excesses of starting materials.

The products from use of the process of the present invention are donor-terminated, have polydispersity approximating that of the starting materials, are Newtonian in shear, and are suited for further elaboration to make a variety of useful products ranging from adhesives to lubricants. They also possess advantages in color, odor, and functional density.

Group IA and/or Group IIA Metal Ion Catalyst:

Because soluble catalyst is preferred, it is most preferred that the lithium ions be introduced as the salt LiBr, soluble in a variety of polar organic Michael donors. Of second preference are sodium or potassium ion-containing salts such as $NaOCOCH_3$ or $K_2CO_3$. Salts such as $CaBr_2$, $Mg(OCOCH_3)_2$, and $Ba(OH)_2$ are also effective but their polyvalent cation nature may interfere with future use of the products, as they are capable of bridging anions that may arise from, for example, hydrolysis of esters, causing an increase in viscosity.

The level of Group IA and/or Group IIA ions, used in combination with another basic catalyst is preferably at least 50 mole percent based on the basic component of the catalyst and more preferably above 100 mole percent to maximize their effectiveness. Lower levels of use will have lesser benefit, and the benefit claimed will disappear at some level of use below 50 mole percent based on the basic component. In choosing the basic component of the catalyst, bases that strongly coordinate the Group IA and/or Group IIA ions or act as nucleophiles capable of uncatalyzed Michael addition should be avoided.

An effective metal ion catalyst may also be formed in-situ, for example by reaction of lithium bromide with an epoxide. In this way a slow metal ion catalyst (LiBr) may be converted to a rapid metal ion catalyst (LiOCCBr) at some later point in the process by application of heat. The benefit may also be used in subsequent reactions of the product of the first addition where it may be desired to substitute the methine hydrogen selected against in the first step.

Metal ions that are capable of making stable, bidentate, six-membered ring complexes such as those in Groups IIB to VIII (e.g., Ti, Zn, Mn, Ni, . . . ) with d-orbit electrons create non-nucleophilic methylene enolate salts resistant to alkylation. These ions will therefore defeat the effective ions by diverting the enolate to these complexes.

In all cases, the addition of ion-clathrating agents such as crown ethers and cyclic polyamines cause a loss of selectivity. Ligating solvents such as polyethers are also capable of destroying the desired selectivity. Accordingly, the reaction of the present invention is preferably carried out in the absence of coordinating amines (such as but not limited to diisopropylamine or tetramethyl ethylene diamine) and ligating solvents (such as dimethoxyethane (DME) and diglyme).

Without limitation by theory, these observations can be understood if the mechanism of action of the effective ions is the creation of ion-paired multi-ion complexes solvated by the acceptor. It is proposed that the near covalent nature of the Li-oxygen bond in the starting enolate in this complex polyion can be transferred to the alpha-beta unsaturated carbonyl oxygen in the Michael addition product to generate a substituted ion pair. An electrocyclic transition state of 2s+2s+2a+2s symmetry can be considered for coordinated Michael addition. This transition state is strongly affected by reagent stereochemistry, and models indicate that substitution at the enolate carbon will be sterically unfavorable for this transition state. Alternatively, the lesser propensity of substituted enolates to form polyion aggregates with the counterion might also explain the selectivity, as these enolate salts will have a lesser tendency to form acceptor/enolate complexes of the type we propose in the course of a second substitution. Thus it is proposed that it is the presence of the acceptor in the complex ionic salts with unsubstituted enolates that provides the selective addition to form a new substituted enolate that dissociates from the complex. To our knowledge, this association/disassociation catalytic mechanism for Michael addition has not previously been discussed in the literature.

Michael Donor and Acceptor Compounds

The Michael donor can be any structure containing the following atom choices in parenthesis ((H, C, O, N, S)—(C, S)=(O, N—)—, H—, C—, O—, X—)CH2-(C, S)=(O, N—) (H, C, O, N, S) where X is any heteroatom electron-withdrawing group. The structure may be linear or cyclic but must contain at least one multiply-bonded heteroatom beta to the $CH_2$ to which an ion in Group IA and/or Group IIA can coordinate. The simplest Michael donors are aldehydes and ketones. The most preferred are 1,3-dicarbonyl compounds of which acetoacetyl esters are common examples.

The Michael acceptor can be any structure containing the following atom choices in parenthesis (C,H)C=CH—C=(S, O, N—) (H, C, O, N, S). The structure may be linear or cyclic but must contain at least one multiply-bonded heteroatom beta to the C=C unsaturation to which an ion in Group IA and/or Group IIA can coordinate. The simplest Michael acceptors are alpha-beta unsaturated aldehydes and ketones. The most preferred are acrylates.

The Michael acceptors are intended to be predominately polyfunctional and include materials that are at least difunctional on average such as triethylene glycol diacrylate or hexanediol diacrylate. In this case, the polydispersity will be in linear molecular weight when difunctional donors such as acetoacetyl esters are also used. The bigger problem in rapid growth of molecular weight occurs when using higher functional acceptors such as trimethylolpropane triacrylate (TMPTA, trifunctional) or pentaerythritol tetraacrylate (PETA, tetrafunctional) where highly branched structures are formed and gelation is possible. These latter often contain difunctional and even some monofunctional ester alcohols as impurities. The inclusion of monofunctional materials may also be intentional to provide terminal groups carrying special functions for further elaboration (e.g., alcohol groups for water compatibility) without loss of our intended benefit if the average acceptor functionality is equal to or larger than two.

The most commonly used donors are naturally polyfunctional in the sense that each activated methylene contains two acidic protons. There may be occasions when the donors are of higher functionality in the sense of containing multiple donor methylenes, for example, in the bis- and tri-acetoacetate esters of glycerol. When these are used, the intent of the reaction described is to remove all the acceptor functionality by Michael addition leaving predominately monosubstituted (methine) donor functions and unsubstituted (methylene) donor functions in the product.

Monofunctional substituted donors such as beta-alkyl-1,3-diketones or beta-hydroxylalkyl-1,3-diketones may be intentionally used to impart special properties via terminal groups without loss of the intended benefit if the average donor functionality of the mixed donors is described by a methylene group. Difunctional structures such as the diesters of 2,5-dicarboxycylcohexane-1,4-dione would be treated as two monofunctional substituted structures in calculation of the average functionality as this sort of polyfunctionality is not addressed by this invention.

Process:

Preferably, the donor in 10% equivalent excess (1.1 equivalent donor $CH_2$ to 1.0 equivalent $CH=CH_2$) is charged to the reactor, and the catalyst components and oxidation stabilizers are added. After bringing this stirred and air-sparged mixture to 55° C., the acceptor is preferably added at a rate that maintains the reactor temperature below 80° C. The reaction goes to completion as monitored by the loss of unsaturation as detected by infrared spectroscopy (or any other monitor of reaction) in the course of 1-4 hours total elapsed time above 65° C. The preferred order of addition of Michael acceptor to Michael donor and enolate establishes a statistical benefit and avoids acceptor transesterification to the greatest possible extent to minimize odor.

To be successful in controlling the selectivity of reaction, the Group IA and/or Group IIA ion or ions need to be dissolved in the reaction medium or at least to be provided to the soluble metal ion catalyst in the preferred 1:1 mole ratio. Preformation of the enolate at a catalytic level is preferred as this most readily accomplishes the formation of the fully assembled catalyst complex. However, as long as the fully assembled catalyst complex forms at the rate needed, the components may start the process largely insoluble in the donor charge and dissolve as the acceptor is added. The final catalyst solubility required is at least 0.01 molal, more preferably >0.1 molal, and most preferably >1.0 molal.

No solvent is needed, but water may be present and may affect catalyst solubility. To avoid bias, we added water up to a small mole fraction in the examples which follow (typically less than 10 mol %) to account for the possibility that commercial starting materials might not be thoroughly dried and that the catalyst components come with varying amounts of waters of hydration. Water content affects the rate and extent of reaction, higher concentrations generally favoring higher extent of conversion. However, water at this level does not affect the product selectivity (and therefore the polydispersity and molecular weight). Also at this level of water, hydrolysis of the ester groups on either of the starting materials or the product is not problematic.

The use level of the effective metal catalysts is preferably above 0.1 mole % based on the moles of donor, more preferably above 0.3 mole %. The use level is adjusted primarily to avoid a strong exotherm and subsequent overheating of the contents of the reactor. The desire is to maintain the reactor below 80° C. to avoid side reactions (e.g., free radical polymerization of the acrylates, aldol condensation at the ketone, hydrolysis, transesterification, etc.). Selectivity may be improved by maintaining a lower temperature, but a convenient process is aided by completion of the reaction in two to four hours. Green processes need to avoid excessive energy consumption to either heat or cool a reactor. All these can be achieved by correct choice of catalyst concentration. The reaction selectivity described herein is independent of catalyst concentration or reaction rate.

Figure 1:
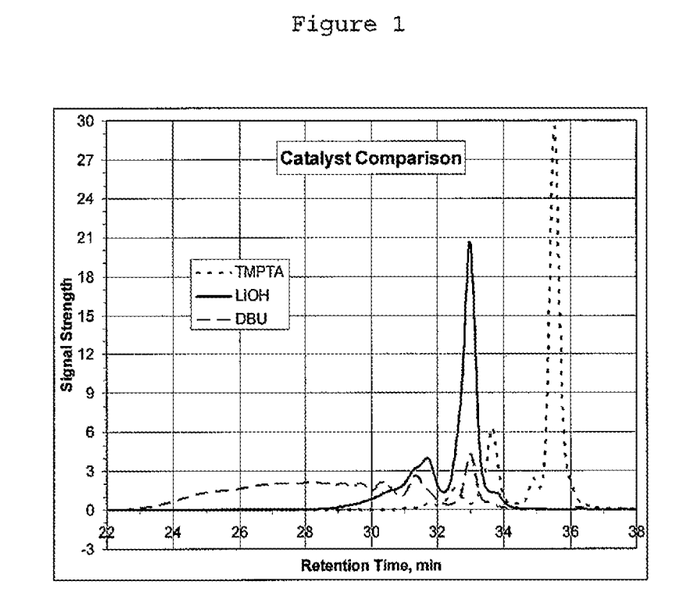
FIG. 1 shows the gel permeation chromatograms of the starting acceptor (TMPTA), the product made from this acceptor according to the present invention along with a small equivalent excess of ethyl acetoacetate with lithium ion and an inorganic base catalyst, and the product available from all other reported procedures using this pair of starting materials (e.g., DBU catalyzed result shown but typical of trioctyl phosphine and Amine/epoxy catalysts also) at this stochiometry but without a Group IA or IIA ion. The comparative example contains oligomers with molecular weights well above 10,000 amu and small amounts above 100,000 amu. These are absent in the product made according to the present invention.

Product:

The low degree of polydispersity is the most attractive and unique feature of the product from this process. The molecular weight distributions can be seen in gel permeation chromatograms where molecular weights are assigned by use of standards (FIG. 1). The structural origins of this distribution can be seen in C13 NMR spectra by measuring the relative abundance of the methine carbon from mono-substitution to the quaternary carbon from di-substitution FIG. 2). The resulting low viscosity liquids from the inventive process can easily be transformed in subsequent reactions to further derivatize the core structure. Although efforts were made to select for the methylene hydrogen in the presence of methine hydrogens, the methine can also be used in a subsequent Michael addition under more forcing conditions. For instance, increased heat or the application of ion clathrates to restore a solvent-separated ion pair can cause the second addition to be conveniently made. A particularly attractive example of the latter would be to carry out the first reaction with $K^+$ as sole ion followed by addition of a quaternary amine salt to restore the original high reactivity of the methine. The low color of the product from our catalyst and process is evidence of less aldol and other unsaturation-producing processes than is the case with other catalysts. The low odor is evidence of little hydrolysis (or transesterification when alcohol functions are also present).

Accordingly, this product is recognized by its low preferred polydispersity (Mw/Mn of less than about 2 compared to the published procedures which generate Mw/Mn>3.5), high functional density (more than about 3 meq/gm), high symmetry, Newtonian viscosity, low color, and low odor.

Example 1

Into a 4-neck 1 liter round bottom flask fitted with a mechanical stirrer, a dip tube for air sparge, a pressure-equalizing dropping funnel, and a temperature probe was added ethyl acetoacetate (107.35 g; Eastman), MEHQ (0.107 g), a radical stabilizer, and a 20 wt % aqueous solution of lithium hydroxide (1.30 g). The mixture was heated to about 60° C. whereupon trimethylolpropane triacrylate (74.0 g; Cognis) was added from the dropping funnel at a rate sufficient to maintain the reaction temperature between 70° C.-80° C. (about 0.6 ml/min). After the addition was complete, the dropping funnel was removed and the mixture was held at 75° C.-80° C. for another 2 hours. Analysis of this intermediate product by both FTIR and GPC revealed no residual olefin. The reaction was quenched by addition of 120 mol % (on the LiOH charged) of $H_2SO_4$ as a 15% aqueous solution. In Table I below (see Sample 1), this product shows a polydispersity of 1.14 and was 90% complete at 75° C. in 165 minutes. Carbon NMR shows less than 2.5% disubstitution at the beta-dicarbonyl methylene carbon in Table II.

Examples 2-6

Effect of Solvent

These examples were prepared as in Example 1 but with the indicated amounts of added solvent prior to addition of the acrylate. They show that strongly coordinating solvents as are often employed in the literature degrade selectivity.

Examples 8 and 14

Effect of Changing Counterion in the Series Li, Na, K

These examples were prepared as in Example 1 with comparable mole % of each hydroxide. The measured polydispersity increases in the order of Li, Na and K (see Samples 1, 8 and 14 in Table I). All examples containing Li and Na are preferred and Li most preferred to yield the highest degree of selectivity.

Examples 9, 11, 14 and 16

Effect of Base Strength

These examples, prepared as in Example 1 but with potassium at variable mole %, were made to compare the effect of base strength of the catalyst precursor in the order acetate, carbonate, hydroxide, and tertiary butoxide on product selectivity. Although varying in rate of reaction by a factor of ten, the base strength of the solution apparently has no bearing on the degree of substitution as measured by the polydispersity (see Samples 9, 11, 14 and 16 of Tables I and II).

Examples 11, 12 and 13

Effect of Ion Coordination

These examples were prepared as in Example 1 but with potassium carbonate starting base to which was added in one case a crown ether and in another a quaternary ammonium chloride salt, both in equi-molar amounts with respect to the potassium. The 18-crown-6 removes the potassium ion from tight coordination with the enolate oxygen causing a doubling of the polydispersity. The quaternary ammonium chloride may substitute chloride for the enolate in the complex ion and produce free enolate that is even less selective (see Samples 11, 12 and 13 of Tables I and II).

Examples 7 and 10

Effect of Li on Phase Transfer Catalysed Michael Addition

Example 7 shows the positive effect of Li ion compared to K in a phase transfer catalyzed reaction. The average mw and polydispersity is halved by addition of Li ion in place of potassium, an effect that is even more dramatic when the base strength is increased as in Example 13.

Examples 14 and 15

Effect of the Order of Addition

Example 15 was run with addition of the donor ethyl acetoacetate to the catalyst contained in TMPTA. The polydispersity in 15 is degraded from the more statistically driven order in Example 14 but is still small (see Samples 14 and 15 of Tables I and II). A result intermediate between these two could be expected from an all-in-one example with a jacketing bath capable of moderating the exotherm.

Examples 17, 18, 19, 20, 21 and 22

Examples with Diazabicycloundecene (DBU)

Figure 2:
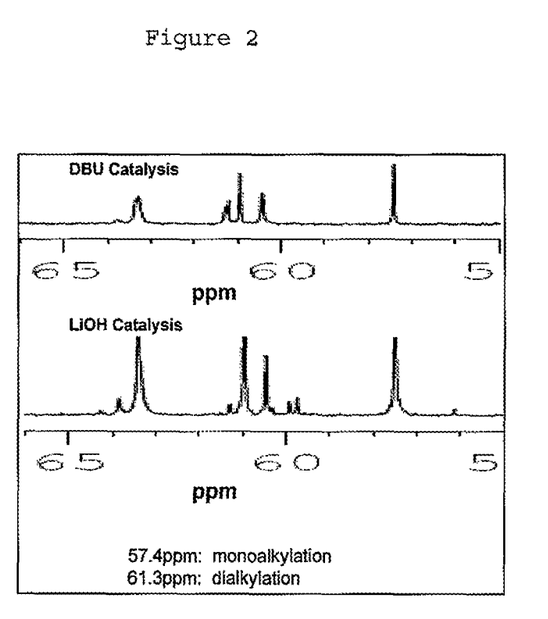
FIG. 2 shows the C13 nmr of the acyl-substituted carbon (flanked by two carbonyl carbons) of the donor portion of the oligomer in both the inventive (lithium ion and an inorganic base) and comparative (DBU) examples shown in FIG. 1, demonstrating the very low proportion of disubstituted carbon in the inventive product.

These examples were prepared as in Example 1 but with the amidine base, DBU. Example 18 uses this common Michael addition catalyst alone to provide a counterexample with high polydispersity as illustrated in FIG. 1. The C13 NMR of this product shows over 30% of disubstitution at the beta-dicarbonyl methylene as illustrated in FIG. 2. The addition of LiBr in Example 19 and to a lesser extent the addition of potassium acetate in Example 17 reverse the effect by formation of the catalytic tight ion pair complex ion of the present invention. However, addition of other salts such as zinc or manganese acetates completely stop the reaction, perhaps by formation of noncatalytic acetoacetyl complexes with these Group B metals (see Samples 17, 18, 19, 20, 21 and 22 of Tables I and II).

Examples 23 and 24

Examples with Trioctylphosphine Catalysts

These examples were prepared as in Example 1 but with a phosphine base. The latter is thought to catalyze via formation of zwitterions from addition to the enol. But whatever the mechanism, the product distribution in Example 23 is broad, a consequence of weak anion coordination. However, in Example 24 which includes LiBr in equimolar amount to the phosphine, a narrow product distribution is restored (see Samples 23 and 24 of Tables I and II).

Examples 25 and 26

Examples with Glycidylmethacrylate

These examples were prepared as in Example 1 but with the combination of an epoxy and a source of a nucleophile as base. In Example 25, the nucleophile is bromide from tetrabutylammonium bromide which opens the epoxy ring to generate a steady state concentration of alkoxide ion. The result is one of the least selective reactions due to a lack of coordination of the enolate by the tetrabutylammonium ion. The free enolate is not selective as we have discussed. But when LiBr is used to form the same alkoxide ion, the result is one of the most selective reactions (see Samples 25 and 26 of Tables I and II).

Examples 27 and 28

Examples with Quaternary Ammonium Hydroxide

These examples were prepared as in Example 1 but with benzyltrimethylammonium hydroxide as base. When this base is used alone, the result is free enolate and lack of selectivity in Sample 27 (Table I). But when LiBr is added in equimolar amount to this catalyst, the result changes back to a high degree of selectivity from formation of the coordinated lithium complex salt (see Sample 28 of Tables I and II).

Examples 29 and 32

Examples with Group IIA Ions

These examples illustrate that the effect of Li and Na ions can be achieved with Group IIA ions also. The best of these is barium, capable of achieving results similar to those of lithium in molecular weight and polydispersity (see Table I). The only drawback to the use of these ions is the possible influence they may have in formulated products where some hydrolysis of esters has occurred. In this case, gels could form from the catalyst residue.

Examples 30 and 31

Effect of High Water Content

With no other change but increased water level, these examples demonstrate the absence of an effect of water on the selectivity and only a minor effect on the yield of the reaction yield (three- to ten-fold increase in residual unsaturation) when barium ion is present.

TABLE I

| Notebook Number | Sample Number | Catalyst[1] type | mol % | Water mol % | Additive[2] type | mol % | EtOAcAc equivs | TMPTA mol % | Residual % C=C[3] | $T_{90}$, 75° C. minutes[4] | GPC Data[5] | | |
|---|---|---|---|---|---|---|---|---|---|---|---|---|---|
| | | | | | | | | | | | $M_n$ | $M_w$ | PD |
| TMPTA | | | | | | | | | 100 | | 328 | 373 | 1.14 |
| | 1 | LiOH | 0.38 | 3.95 | | | 1.650 | 0.454 | 2.1 | 165 | 762 | 900 | 1.18 |
| | 2 | | 0.50 | 4.75 | THF | 60.6 | 1.650 | 0.455 | baseline | 185 | 778 | 911 | 1.17 |
| | 3 | LiOH | | | EGDME | | | | | | | | |
| | 4 | LiOH | 0.29 | 1.46 | DiGlyme | 1.17 | 1.650 | 0.454 | baseline | <60 | 933 | 1324 | 1.42 |
| | 5 | LiOH | 0.32 | 1.60 | TMEDA | 0.76 | 1.650 | 0.455 | baseline | <60 | 933 | 1315 | 1.41 |

TABLE I-continued

| Notebook Number | Sample Number | Catalyst[1] type | mol % | mol % Water | Additive[2] type | mol % | EtOAcAc equivs | TMPTA mol % | Residual % C=C[3] | T₉₀, 75° C. minutes[4] | GPC Data[5] $M_n$ | $M_w$ | PD |
|---|---|---|---|---|---|---|---|---|---|---|---|---|---|
| | 6 | LiOH | 0.32 | 1.59 | HMPTA | 1.16 | 1.650 | 0.455 | baseline | <60 | 945 | 1346 | 1.42 |
| | 7 | LiOH | 0.58 | 2.56 | MeTBACl | 0.58 | 1.650 | 0.455 | baseline | <60 | 741 | 901 | 1.21 |
| | 8 | NaOH | 0.36 | 0.96 | | | 1.651 | 0.454 | baseline | <60 | 822 | 1001 | 1.22 |
| | 9 | KOAc | 0.95 | 7.16 | | | 1.650 | 0.454 | 2.2 | >600 | 934 | 1314 | 1.41 |
| | 10 | | 0.95 | 7.60 | MeTBACl | 0.95 | 1.650 | 0.455 | baseline | <60 | 1768 | 4574 | 2.59 |
| | 11 | K₂CO₃ | 0.39 | 3.01 | | | 1.650 | 0.456 | baseline | <60 | 915 | 1263 | 1.38 |
| | 12 | | 0.39 | 2.91 | 18-c-6 | 0.39 | 1.649 | 0.455 | baseline | 60 | 1769 | 4463 | 2.52 |
| | 13 | | 0.46 | 3.57 | MeTBACl | 0.46 | 1.651 | 0.454 | baseline | 240 | 2525 | 8964 | 3.55 |
| | 14 | KOH | 0.35 | 1.51 | | | 1.650 | 0.455 | baseline | <60 | 943 | 1304 | 1.38 |
| | 15 | | 0.32 | 1.25 | inverse addition | | 1.650 | 0.455 | 3.5 | >500 | 1118 | 1900 | 1.70 |
| | 16 | KOtBu | 0.37 | | | | 1.650 | 0.456 | baseline | <60 | 844 | 1157 | 1.37 |
| | 17 | DBU | 0.38 | 5.42 | KOAc | 0.72 | 1.650 | 0.455 | 1.2 | 70 | 1405 | 2871 | 2.04 |
| | 18 | | 0.39 | | | | 1.650 | 0.455 | 2.6 | 125 | 2156 | 7398 | 3.43 |
| | 19 | | 0.37 | | LiBr | 0.38 | 1.650 | 0.456 | 2.9 | 230 | 850 | 1048 | 1.23 |
| | 20 | | 0.35 | 4.55 | AgOAc | 0.38 | 1.650 | 0.06 | GEL | | | | |
| | 21 | | 0.38 | 9.61 | Zn(OAc)₂ | 0.38 | 1.650 | 0.455 | ~81 | 5,000 | — | — | — |
| | 22 | | 0.38 | 5.59 | Mn(OAc)₂ | 0.38 | 1.650 | 0.455 | GEL | | | | |
| | 23 | TOP | 0.37 | | | | 1.650 | 0.455 | baseline | <60 | 1806 | 5047 | 2.80 |
| | 24 | | 0.37 | | LiBr | 0.38 | 1.650 | 0.455 | baseline | 230 | 847 | 1035 | 1.22 |
| | 25 | GMA | 0.38 | | TBABr | 0.37 | 1.650 | 0.455 | baseline | 150 | 2366 | 9537 | 4.03 |
| | 26 | | 0.38 | | LiBr | 0.39 | 1.650 | 0.455 | baseline | 165 | 804 | 953 | 1.18 |
| | 27 | BzNMe₃OH | 0.37 | | | | 1.650 | 0.455 | baseline | 60 | 2306 | 8430 | 3.66 |
| | 28 | | 0.37 | | LiBr | 0.37 | 1.650 | 0.455 | 2.2 | 235 | 784 | 930 | 1.19 |
| | 29 | Ca(OH)₂ | 0.36 | 2.48 | | | 1.650 | 0.456 | 3.0 | 820 | 874 | 1191 | 1.36 |
| | 30 | Ba(OH)₂ | 0.36 | 18.66 | | | 1.650 | 0.455 | ~10 | 90 | 739 | 872 | 1.18 |
| | 31 | | 0.38 | 9.60 | | | 1.650 | 0.455 | 2.9 | 90 | 792 | 944 | 1.19 |
| | 32 | | 0.38 | 3.07 | | | 1.650 | 0.455 | 1.5 | 90 | 826 | 999 | 1.21 |

[1]LiOH Lithium hydroxide hydrate
NaOH Sodium hydroxide
KOAc Potassium acetate hydrate
K₂CO₃ Potassium carbonate
KOH Potassium hydroxide
KOtBu Potassium tert-butoxide
DBU Diazabicycloundecene
TOP Trioctylphosphine
GMA Glycldylmethacrylate
BzNMe₃OH Benzyltrimethylammonium hydroxide
Ca(OH)₂ Calcium hydroxide
Ba(OH)₂ Barium hydroxide octahydrate
[2]18-c-6 18-crown-6
THF Tetrahydrofuran
EGDME Ethyleneglycol dimethyl ether
DEGDME Diethyleneglycol dimethyl ether
TMEDA Tetramethylethylenediamine
HMPA Hexamethylphosphoramide
DMSO Dimethylsulfoxide
MeTBACl Methyltributylammonium chloride
TBABr Tetrabutylammonium bromide
LiBr Lithium bromide
KOAc Potassium acetate hydrate
Zn(OAc)₂ Zinc diacetate dihydrate
Mn(OAc)₂ Manganese acetate tetrahydrate
AgOAc Silver acetate
[3]Estimated from peak-to-trough height of first derivative of FTIR 811 cm⁻¹ C=C—H signal at T = 0 (uncatalyzed)
[4]Estimated from semilog plot of residual C=C concentration (of in-process samples) vs elapsed reaction time
[5]Based on polystyrene standards run in THF on a 10⁴ A, 10³ A, 10² A, 50 A column set using a Waters GPC system

TABLE II

| Notebook Number | Sample Number | Catalyst[1] type | mol % Water | Additive[2] type | EtOAcAc equivs | TMPTA mol % | GCS[3] # | Visc.[4] Pa·s. | 13CNMR[5] mono | di |
|---|---|---|---|---|---|---|---|---|---|---|
| | 1 | LiOH | 3.95 | | 1.650 | 0.454 | 3.5 | 0.399 | 97.6 | 2.4 |
| | 2 | | 4.75 | THF | 1.650 | 0.455 | 3 | | | |
| | 3 | LiOH | | EGDME | | | | | | |
| | 4 | LiOH | 1.46 | DiGlyme | 1.650 | 0.454 | 4 | | | |
| | 5 | LiOH | 1.60 | TMEDA | 1.650 | 0.455 | 4.5 | | | |
| | 6 | LiOH | 1.59 | HMPTA | 1.650 | 0.455 | 4.5 | | | |
| | 7 | | | MeTBACl | 1.650 | 0.455 | 5 | 0.422 | | |
| | 8 | NaOH | 0.96 | | 1.651 | 0.454 | 5 | 0.449 | 96.2 | 3.8 |
| | 9 | KOAc | 7.16 | | 1.650 | 0.454 | 7 | 0.586 | 92.2 | 7.8 |

TABLE II-continued

| Notebook Number | Sample Number | Catalyst[1] type | mol % Water | Additive[2] type | EtOAcAc equivs | TMPTA mol % | GCS[3] # | Visc.[4] Pa·s | 13CNMR[5] mono | 13CNMR[5] di |
|---|---|---|---|---|---|---|---|---|---|---|
| | 10 | | 7.60 | MeTBACl | 1.650 | 0.455 | 7 | 0.844 | | |
| | 11 | K₂CO₃ | 3.01 | | 1.650 | 0.456 | 8 | 0.445 | | |
| | 12 | | 2.91 | 18-c-6 | 1.649 | 0.455 | 11 | 1.383 | 74.9 | 25.1 |
| | 13 | | 3.57 | MeTBACl | 1.651 | 0.454 | 10 | 1.056 | | |
| | 14 | KOH | 1.51 | | 1.650 | 0.455 | 9 | 0.56 | 91.8 | 8.2 |
| | 15 | | 1.25 | Inverse Additiion | 1.650 | 0.455 | 6 | 0.677 | | |
| | 16 | KOtBu | | | 1.650 | 0.456 | 14 | 0.437 | 92.8 | 7.2 |
| | 17 | DBU | 5.42 | KOAc | 1.650 | 0.455 | 8 | 0.779 | 78.8 | 21.2 |
| | 18 | | | | 1.650 | 0.455 | 9 | 2.556 | 70.1 | 29.9 |
| | 19 | | | LiBr | 1.650 | 0.456 | 2 | 0.528 | 96.3 | 3.7 |
| | 20 | | 4.55 | AgOAc | 1.650 | 0.06 | | | | |
| | 21 | | 9.61 | Zn(OAc)₂ | 1.650 | 0.455 | | | | |
| | 22 | | 5.59 | Mn(OAc)₂ | 1.650 | 0.455 | | | | |
| | 23 | TOP | | | 1.650 | 0.455 | 11 | 2.227 | 73.2 | 26.8 |
| | 24 | | | LiBr | 1.650 | 0.455 | 4 | 0.603 | 97.5 | 2.5 |
| | 25 | GMA | | TBABr | 1.650 | 0.455 | 4 | 3.115 | 70.2 | 29.8 |
| | 26 | | | LiBr | 1.650 | 0.455 | 1 | 0.626 | 97.8 | 2.2 |
| | 27 | BzNMe₃OH | | | 1.650 | 0.456 | 11 | 1.745 | 68.6 | 31.4 |
| | 28 | | | LiBr | 1.650 | 0.455 | 3 | 0.462 | 97.5 | 2.5 |
| | 29 | Ca(OH)₂ | 2.48 | | 1.650 | 0.456 | 7 | 2.08 | | |
| | 30 | Ba(OH)₂ | 18.66 | | 1.650 | 0.455 | 4 | 0.669 | | |
| | 31 | | 9.60 | | 1.650 | 0.455 | 4 | 0.722 | | |
| | 32 | | 3.07 | | 1.650 | 0.455 | 4 | 0.895 | | |

[1]LiOH Lithium hydroxide hydrate
NaOH Sodium hydroxide
KOAc Potassium acetate hydrate
K₂CO₃ Potassium carbonate
KOH Potassium hydroxide
KOtBu Potassium tert-butoxide
DBU Diazabicycloundecene
TOP Trioctylphosphine
GMA Glycidylmethacrylate
BzNMe₃OH Benzyltrimethylammonium hydroxide
Ca(OH)₂ Calcium hydroxide
Ba(OH)₂ Barium hydroxide octahydrate
[2]18-c-6 18-crown-6
THF Tetrahydrofuran
EGDME Ethyleneglycol dimethyl ether
DEGDME Diethyleneglycol dimethyl ether
TMEDA Tetramethylethylenediamine
HMPA Hexamethylphosphoramide
DMSO Dimethylsulfoxide
MeTBACl Methyltributylammonium chloride
TBABr Tetrabutylammonium bromide
LiBr Lithium bromide
KOAc Potassium acetate hydrate
Zn(OAc)₂ Zinc diacetate dihydrate
Mn(OAc)₂ Manganese acetate tetrahydrate
AgOAc Silver acetate
[3]Gardner Color Scale
[4]Shear viscosity, 10 s-1, 25 C., AR1000 4 cm 2 deg cone and plate
[5]from integration of peaks identified in DEPT spectra obtained in d8-THF The invention has been described in terms of preferred embodiments thereof, but is more broadly applicable as will be understood by those skilled in the art. The scope of the invention is only limited by the following claims.

What is claimed is:

1. A method of preparing an oligomeric or polymeric compound in a liquid solution only via monosubstitution by reacting a Michael donor compound containing at least one acidic methylene group with an unsaturated Michael acceptor compound containing more than one unsaturated group in the presence of a first catalyst and a Group IA and/or Group IIA metal ion catalyst, wherein said first catalyst does not comprise said metal ions.

2. The method of claim 1, wherein said Michael donor compound and Michael acceptor compound have an equivalent ratio of about 1:1.

3. The method of claim 1, wherein said Michael donor compound comprises at least one multiply-bonded heteroatom beta to a $CH_2$ group to which an ion in Group IA and/or Group IIA can coordinate.

4. The method of claim 1, wherein said Michael donor compound is linear or cyclic.

5. The method of claim 1, wherein said Michael donor compound is an aldehyde or ketone.

6. The method of claim 1, wherein said Michael donor compound is a 1,3-dicarbonyl compound.

7. The method of claim 1, wherein said Michael donor compound is an acetoacetyl ester.

8. The method of claim 1, wherein said Michael acceptor compound comprises at least one multiply-bonded heteroatom beta to a C=C unsaturated group to which an ion in Group IA and/or Group IIA can coordinate.

9. The method of claim 1, wherein said Michael acceptor compound is linear or cyclic.

10. The method of claim 1, wherein said Michael acceptor compound contains carbon to carbon multiple bonds attached directly to one or more electron withdrawing groups.

11. The method of claim 1, wherein said Michael acceptor compound is an alpha-beta unsaturated aldehyde or ketone.

12. The method of claim 1, wherein said Michael acceptor compound is an acrylate compound.

13. The method of claim 1, wherein said Michael acceptor compound is a polyacrylate compound.

14. The method of claim 1, wherein said Michael acceptor compound is selected from the group consisting of vinyl ketones, maleate esters, fumarate esters, acetylene dicarboxylate esters, acrylonitrile derivatives, vinyl sulfones, vinyl sulfonates and nitro olefins.

15. The method of claim 1, wherein said Group IA and/or Group IIA metal ion is selected from the group consisting of: $Li^+$, $K^+$, $Na^+$, and $Ba^+$.

16. The method of claim 15, wherein said Group IA and/or Group IIA metal ion is $Li^+$.

17. The method of claim 1, wherein said Group IA and/or Group IIA metal ion is in the form of a salt.

18. The method of claim 17, wherein said salt is LiBr.

19. The method of claim 17, wherein said salt is $BaCl_2$.

20. The method of claim 1, wherein said first catalyst is a base catalyst.

21. The method of claim 20, wherein said metal ion catalyst is present in an amount of at least 50 mole percent based on the basic component of the base catalyst.

22. The method of claim 20, wherein said metal ion catalyst is present in an amount of at least 100 mole percent based on the basic component of the base catalyst.

23. The method of claim 20, wherein said base catalyst is an amidine or phosphine base.

24. The method of claim 23, wherein said base catalyst is Diazabicycloundecene (DBU), DBN and TOP.

25. The method of claim 1, wherein said reaction occurs in the absence of a coordinating amine.

26. The method of claim 25, wherein said coordinating amine is diisopropylamine or tetramethyl ethylene diamine.

27. The method of claim 1, wherein said reaction takes place in the absence of a ligating solvent.

28. An oligomeric or polymeric compound prepared by the method of claim 1.

29. The compound of claim 28 having a polydispersity (Mw/Mn) of less than about 2.

30. The compound of claim 28 having a high functional density of more than about 3 meq/gm.

* * * * *